United States Patent [19]
Duckett et al.

[11] Patent Number: 6,007,824
[45] Date of Patent: Dec. 28, 1999

[54] NATURAL COMPOSITION AND METHOD FOR THE TREATMENT OF SEXUAL DYSFUNCTION

[76] Inventors: Melvin J. Duckett, 16300 Cedar Grove Rd., Sparks, Md. 21152; Kyle Moore, 4705 Creekside Cir., Apt. 13, Owings Mills, Md. 21117

[21] Appl. No.: 09/255,587

[22] Filed: Feb. 22, 1999

Related U.S. Application Data

[60] Provisional application No. 60/092,143, Jul. 9, 1998.

[51] Int. Cl.⁶ .......................... A61K 35/78; A61K 39/385
[52] U.S. Cl. .......................................... 424/195.1; 514/565
[58] Field of Search ........................... 424/195.1; 514/565

[56] References Cited

PUBLICATIONS

Chevallier, A., The Encyclopedia of Medicinal Plants, New York: DK, 1996, pp. 281 and 316.

*Primary Examiner*—M Moezie
*Attorney, Agent, or Firm*—Law Offices of Royal W. Craig

[57] ABSTRACT

A composition and method for treating sexual dysfunction by natural means using a combination of L-arginine, ginseng and Zizyphi fructus in an orally administered dosage. The combination works synergistically to alleviate erectile dysfunction by stimulating enough release of NO in the corpus cavernosum to produce and sustain smooth muscle relaxation, thereby allowing the inflow of blood and alleviating erectile dysfunction. Thus, a natural medicinal alternative to Viagra® is provided for the treatment of erectile dysfunction. The composition and method is also useful in treating sexual conditions in females.

15 Claims, 2 Drawing Sheets

NATURAL COMPOSITION AND METHOD FOR THE TREATMENT OF SEXUAL DYSFUNCTION

CROSS-REFERENCE TO RELATED APPLICATIONS

The present application is based on provisional application no. 60/092,143, filed Jul. 9, 1998.

BACKGROUND OF THE INVENTION

1. Field of the invention

The present invention relates to the treatment of sexual dysfunction and, more particularly, to an improved natural composition and method for treatment of erectile dysfunction and female sexual dysfunction using a combination of L-arginine, ginseng and Zizyphi fructus in an orally administered dosage.

2. Description of the Background

The most prevalent type of sexual dysfunction is "Erectile Dysfunction", e.g., "the inability to achieve and/or maintain an erection sufficient for sexual activity" (New England Journal of Medicine). Erectile dysfunction is most often attributable to the inability to generate enough NO in the corpus cavernosum.

The physiologic mechanism of erection of the penis involves release of nitric oxide (NO) in the corpus cavernosum during sexual stimulation. NO then activates the enzyme guanylate cyclase, which results in increased levels of cyclic guanosine monophosphate (cGMP), producing smooth muscle relaxation in the corpus cavernosum and allowing inflow of blood.

There is one well-established solution. Viagra® is an oral drug for erectile dysfunction made by Pfizer, Inc. Viagra® received FDA approval on Mar. 27 1998, and has since Viagra® has given new hope to over 30 million men that suffer from the problem. Viagra® was proven effective in 7 out of 10 men in clinical trials.

Viagra® is the citrate salt of sildenafil, a selective inhibitor of cyclic guanosinemonophosphate (cGMP)-specific phosphodiesterase type 5 (PDE5). Sildenafil citrate is designated chemically as 1-[[3-(6,7-dihydro-1-methyl-7-oxo-3-propyl-1H-pyrazolo [4,3-d]pyrimidin-5-yl)-4-ethoxyphenyl]sulfonyl]-4-methylpiperazine citrate and has the structural formula shown in FIG. 1.

Sildenafil citrate is a crystalline powder, and Viagra® puts this in tablet form equivalent to 25 mg, 50 mg and 100 mg of sildenafil for oral administration. In addition to the active ingredient, sildenafil citrate, each tablet contains the following inactive ingredients: microcrystalline cellulose, anhydrous dibasic calcium phosphate, croscarmellose sodium, magnesium stearate, hydroxypropyl methylcellulose, titanium dioxide, lactose, triacetin, and FD & C Blue #2 aluminum lake.

Sildenafil has no direct relaxant effect on isolated human corpus cavernosum, but enhances the effect of nitric oxide (NO) by inhibiting phosphodiesterase type 5 (PDE5), which is responsible for degradation of cGMP in the corpus cavernosum. When sexual stimulation causes local release of NO, inhibition of PDE5 by sildenafil causes increased levels of cGMP in the corpus cavernosum, resulting in smooth muscle relaxation and inflow of blood to the corpus cavernosum.

Although there are few known side-effects with Viagra®, it is a drug that required full FDA approval, and physicians must prescribe its usage and dosage for their patients.

Unfortunately, a significant stigma is attached to erectile dysfunction, and many of its sufferers simply will not seek medical help. Thus, Viagra® remains unavailable to a large proportion of the affected population. It would be greatly advantageous to provide a natural and organic alternative treatment with the same or similar benefits, but without the same level of risk.

It is known that the same or similar benefits can be achieved by a different mechanism than Viagra®. Again, Viagra® inhibits phosphodiesterase type 5 (PDE5), which slows the degradation of cGMP in the corpus cavernosum. The resulting increased levels of cGMP in the corpus cavernosum results in smooth muscle relaxation. In contrast, it is possible to foster smooth muscle relaxation directly by stimulating the release of NO in the corpus cavernosum during sexual stimulation. The NO in turn is acted upon by the enzyme guanylate cyclase, which results in increased levels of cGMP, again producing smooth muscle relaxation in the corpus cavernosum and allowing inflow of blood. See, e.g., Rajfer et al., *Nitric Oxide as a Mediator of Relaxation of the Corpus Cavernosum in Response to Nonadrenergic, Noncholinergic Neurotransmission,* N. Engl. J. Med., 326 (2), pp. 90-4 (Jan 9, 1992).

Notwithstanding there are relatively few studies that suggest how to stimulate the release of NO in the corpus cavernosum.

It is recognized that NO-nitro-L-arginine is an inhibitor of nitric oxide synthase, and studies have shown that concentrations of NO-nitro-L-arginine (3×10(−S) mol/l) can abolish relaxations. Moreover, the inhibitory effect of NO-nitro-L-arginine can be reversed in the presence of L-arginine (3×10(−3) mol/l). Simonsen et al., *Nitric Oxide Is Involved in the Inhibitory Neurotransmission and Endothelium-dependent Relaxations of Human Small Penile Arteries,* Clin. Sci. (Colch) 92:3, pp. 269–75 (March 1997). This research suggests that L-arginine can be an effective substrate for NO synthase, and may stimulate the release of NO in the corpus cavemosum.

Beside the use of L-arginine, there is little to suggest how to stimulate the release of NO in the corpus cavernosum. It would be greatly advantageous to combine the use of L-arginine with other natural and organic constituents to stimulate enough release of NO in the corpus cavernosum to produce and sustain smooth muscle relaxation in the corpus cavernosum, allowing inflow of blood, and alleviating erectile dysfunction.

It would also be advantageous to provide a composition as described above which is also effective for treating sexual conditions in females. It has been found that clitoral smooth muscle cells include many of the same morphological characteristics as the male corpus cavernosum, and should be physiologically responsive via the same messengers (cGMP) to promote smooth muscle relaxation. Park et al., *Morphological/Biochemical Characterization of Human Corpus Clitoral Smooth Muscle Cells in Culture,* Journal. of Urology, v. 159, n. 5, sup. (June 1998). Thus, that which promotes smooth muscle relaxation in the corpus cavernosum, allowing inflow of blood, and alleviating erectile dysfunction, should work well to alleviate female sexual dysfunction. Indeed, women claim to experience benefit from Viagra® and clinical tests are now being performed.

SUMMARY OF THE INVENTION

It is, therefore, an object of the present invention to provide a natural alternative to Viagra® for the treatment of sexual dysfunction, and for generally increasing sexual performance in both males and females.

It is another object to combine the use of L-arginine with other natural and organic constituents to stimulate increased release of NO in the corpus cavernosum to produce and sustain smooth muscle relaxation in the corpus cavernosum, allowing inflow of blood, and alleviating erectile dysfunction.

According to the present invention, the above-described and other objects are accomplished by providing a combination of L-arginine, ginseng and zizyphi fructus in an orally administered dosage, these ingredients acting synergistically to stimulate enough release of NO in the corpus cavernosum and clitoris. The combination, when administered in proper concentration, works to allow the inflow of sufficient blood to promote smooth muscle relaxation. The effect is sufficient in the corpus cavernosum to sustain smooth muscle relaxation and thereby eliminate erectile dysfunction in many persons. Based on research, it is believed that there will be beneficial results for female sexual dysfunction as well, and the composition will likely provide a remedy for many female conditions.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

Past studies with natural ingredients have shown that a few have a tendency to increase synthesis of NO levels. While these studies have had various purposes, none have dealt with smooth muscle relaxation or sexual dysfunction.

Examples of such studies with natural medicines include ginseng, ginsenoside, and its purified derivative RG1. It has been shown that RG1 enhances the production of NO for killing certain tumor cells. See, e.g., Fan et al., *Enhancement of Nitric Oxide Production from Activated Macrophages by a Purified Form of Ginsenoside (Rg1)*, American Journal of Chinese Medicine, Vol. XXHI, Nos. 3–4. pp. 279–287 (1995 Institute for Advanced Research in Asian Science and Medicine).

Another chinese anti-asthmatic herbal medicine, Zizyphi fructus (jujube), a derivative of Zizyphi Seeds, increases NO production. At least one study viewed the effects of Zizyphi fructus on NO generation on canines and found that Zizyphi fructus caused a concentration-dependent increase in NO. The results suggest that Zizyphi fructus enhances airway (tracheal) ciliary motility and that this effect is exerted through the stimulation of epithelial NO generation. See, Tamaoki et al., *Zizyphi fructus, a Constituent of Antiasthmatic Herbal Medicine, Stimulates Airway Epithelial Ciliary Motility Through Nitric Oxide Generation*, May–June; 22(3):255–66, Exp Lung Res (1996).

The present inventors have found that the combination of Zizyphi fructus and ginseng (or its purified derivative ginsenoside or RG1) as described above, plus L-arginine, work synergistically to stimulate the release of NO in the corpus cavernosum to promote smooth muscle relaxation. Each of the three constituents has an individual tendency to enhance the release of NO in the corpus cavernosum during sexual stimulation. The inventors have found that the synergy stems from a catalyst effect: as illustrated in the flow diagram of FIG. 2 the Zizyphi fructus and ginseng speed up the conversion of L-arginine to NO. Thus, the combination of Zizyphi fructus, ginseng (or its purified derivative ginsenoside or RG1) as described above, plus L-arginine, when administered in proper concentration, stimulate sufficient release of NO in the corpus cavernosum to allow the inflow of blood and alleviate erectile dysfunction. While any of the three constituents taken alone would be insufficient to produce the desired result, in combination they work synergistically to produce significant NO.

Figure 1:
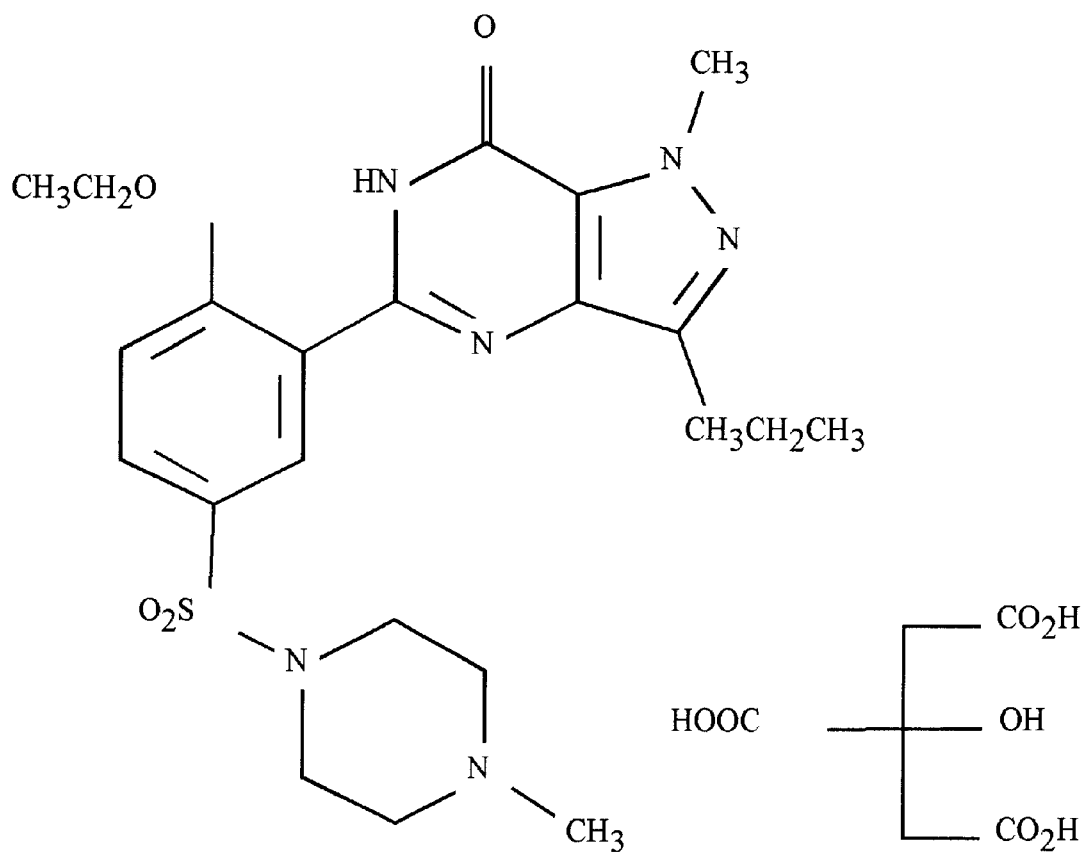
FIG. 1 illustrates the structural formula for Sildenafil citrate (Viagra®).
Figure 2:
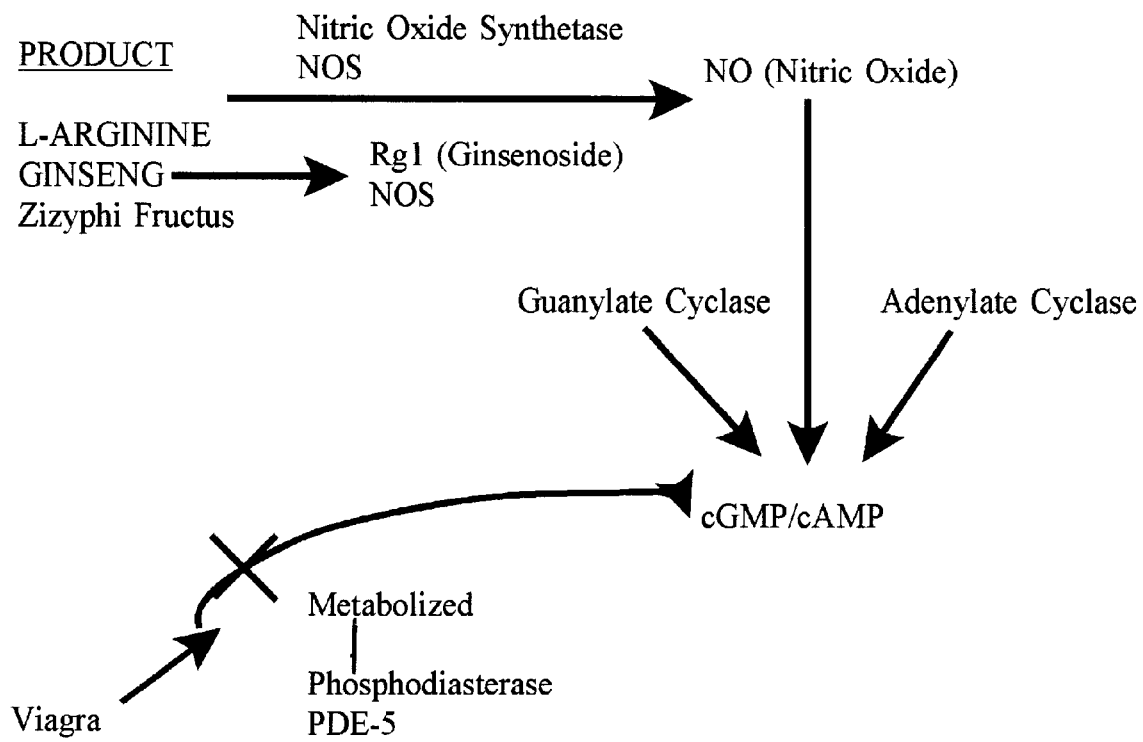
FIG. 2 is a flow diagram showing the comparative mechanisms by which Viagra® and the present invention both stimulate increased levels of cGMP in the corpus cavernosum, resulting in smooth muscle relaxation and inflow of blood.

As seen in the flow diagram of FIG. 2, the additional NO is converted by guanylate cyclase, resulting in increased levels of cyclic guanosine monophosphate (cGMP) in the corpus cavernosum. The cGMP in turn produces smooth muscle relaxation and improves arterial blood flow which results in an improved trapping of blood in the corpus cavernosum. The same mechanism should improve female sexual conditions as well. See Park et al., supra.

It should be understood that the proper relative concentrations of the three constituents may vary depending on the physical characteristics of each person. However, preliminary research suggests that the desired effect is best achieved with a single dose comprising the following preferred concentrations and known acceptable ranges:

L-arginine: 200 mg (within a range of approximately 100–300 mg);

ginseng: 100 mg (within a range of approximately 50–200 mg);

Zizyphi fructus: 7.2 micrograms per mililiter (within a range of +/− 2.9 micrograms per mililiter).[1]

[1] The preferred concentration of Zizyphi fructus is derived primarily from the Tamaoki et al. Article, supra.

Based on research, it is believed that the combination will have similar results in the female urological tract and will likely provide a remedy for many urological conditions.

The combined L-arginine, ginseng and Zizyphi fructus can be administered orally in liquid or tablet form, and thereby provides a safe, convenient and over-the-counter remedy for sexual dysfunction. The three constituents are purely organic, they have no known side-effects and have been time tested for other purposes. The product can be taken without a physician's prescription. Thus, sufferers of erectile dysfunction who choose not to seek medical help have a viable non-prescription alternative.

In the preferred embodiment, additional organic ingredients are added to achieve incidental benefits. For instance, an amount of saw palmetto is added to help the nervous, respiratory and digestive systems. Saw palmetto is especially helpful for overcoming glandular weakness in general and to regenerate sexual glands in particular. It is a well-known dietary aid for increasing male prostate health. Saw palmetto also contains a compound used by the body to manufacture cortisone. Cortisone is an adrenal hormone that helps regulate the metabolism of fats, carbohydrates (for energy), sodium and potassium (again for energy) and proteins, and it helps the body deal with inflammation.

Furthermore, an amount of Gingko Biloba is added. Gingko Biloba is an antioxidant and has been shown to increase blood flow to the brain, and thus improve memory and cognitive functions. Gingko Biloba increases blood flow to heart muscle, and protects that muscle from damage.

Gingko Biloba relieves anxiety and depression, it can help vertigo and tinnitus (ringing in ears), and it may relieve asthma and allergy symptoms.

Glutamic Acid is added as a protein supplement. The ingested protein is hydrolyzed by the digestive system and is then combined into the specific proteins needed for growth and to maintain good health.

An amount of L-Alanine is added as well, as this amino acid aids in the metabolism of glucose (a simple carbohydrate that the body uses for energy).

An amount of L-Lysine may also be included as this protein supplement helps calcium absorption and maintains nitrogen balance.

Of course, in addition to the above-described active ingredients, further inert ingredients may be added as desired to achieve a desired taste, color or consistency.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A composition for alleviating sexual dysfunction, comprising L-arginine, ginseng and Zizyphi fructus, said constituents being administered to stimulate release of NO in the human body to produce smooth muscle relaxation.

2. The composition for alleviating sexual dysfunction according to claim 1, wherein said constituents are are present in the following amounts: a range of approximately 100–300 mg of said L-arginine, a range of approximately 50–200 mg of said ginseng, and a range of approximately 4.3–10.1 micrograms per milliliter of Zizyphi fructus.

3. The composition for alleviating sexual dysfunction according to claim 2, wherein said constituents are resent in the following amounts approximately 200 mg of said L-arginine, approximately 100 mg of said ginseng, and approximately 7.2 micrograms per milliliter of Zizyphi fructus.

4. The composition for alleviating sexual dysfunction according to claim 2, wherein said constituent amounts are formed as a pill for oral administration.

5. The composition for alleviating sexual dysfunction according to claim 2, wherein said constituent amounts are formed as a liquid for oral administration.

6. The composition for alleviating sexual dysfunction according to claim 1, further comprising Saw Palmetto.

7. The composition for alleviating sexual dysfunction according to claim 1, further comprising Ginkgo Biloba.

8. The composition for alleviating sexual dysfunction according to claim 1, further comprising L-Alanine.

9. The composition for alleviating sexual dysfunction according to claim 1, further comprising Glutamic Acid.

10. The composition for alleviating sexual dysfunction according to claim 1, further comprising L-Lysine.

11. A method for treating erectile dysfunction, comprising the steps of:
   combining L-arginine, ginseng, and Zizyphi fructus in a mixture;
   orally administering said mixture to a human to stimulate release of NO in the human body and to thereby produce smooth muscle relaxation.

12. The method for treating erectile dysfunction according to claim 11, wherein said mixture is administered in a single dose including a range of approximately 100–300 mg of said L-arginine, a range of approximately 50–200 mg of said ginseng, and a range of approximately 4.3–10.1 micrograms per mililiter of Zizyphi fructus.

13. The method for treating erectile dysfunction according to claim 12, wherein said dose comprises approximately 200 mg of said L-arginine, approximately 100 mg of ginseng, and approximately 7.2 micrograms per milliliter of Zizyphi fructus.

14. The method for treating erectile dysfunction according to claim 11, wherein said step of combining L-arginine, ginseng, and Zizyphi fructus in a mixture comprises combining said mixture in pill form for oral administration.

15. The method for treating erectile dysfunction according to claim 11, wherein said step of combining L-arginine, ginseng, and Zizyphi fructus in a mixture comprises combining said mixture in liquid form for oral administration.

* * * * *